United States Patent
Anunta

[11] Patent Number: 6,003,510
[45] Date of Patent: Dec. 21, 1999

[54] HAND TOOL FOR INTRODUCING A LARYNGEAL MASK

[76] Inventor: Boonchuay Anunta, 135 Nottingham Ter., Buffalo, N.Y. 14216

[21] Appl. No.: 08/984,940

[22] Filed: Dec. 4, 1997

[51] Int. Cl.[6] .................................................. A61M 16/00
[52] U.S. Cl. ................................. 128/200.26; 128/207.15
[58] Field of Search ..................... 128/200.26, 207.14, 128/207.15; 604/41, 54, 77, 93, 264, 280, 282, 283; 606/108, 196

[56] References Cited

U.S. PATENT DOCUMENTS

| | | |
|---|---|---|
| 465,161 | 12/1891 | Chase . |
| 480,787 | 8/1892 | Scott . |
| 614,854 | 11/1898 | Frank et al. . |
| 724,046 | 3/1903 | Sampson . |
| 1,761,761 | 6/1930 | Vicente . |
| 2,247,258 | 6/1941 | Shepard ..................................... 128/16 |
| 2,657,691 | 11/1953 | Nordstrom, Jr. . |
| 2,723,661 | 11/1955 | Hull ........................................ 128/15 |
| 3,154,069 | 10/1964 | Ring . |
| 3,316,913 | 5/1967 | Swenson . |
| 3,324,849 | 6/1967 | Kravitz . |
| 3,890,960 | 6/1975 | Wunsch et al. ............................ 128/16 |
| 3,930,507 | 1/1976 | Berman . |
| 4,612,927 | 9/1986 | Kruger ................................. 128/200.26 |
| 4,827,910 | 5/1989 | Mathews, III ....................... 128/207.15 |
| 4,982,729 | 1/1991 | Wu ..................................... 128/200.26 |
| 5,024,218 | 6/1991 | Ovassapian et al. .............. 128/200.26 |
| 5,038,766 | 8/1991 | Parker ................................. 128/200.26 |
| 5,042,469 | 8/1991 | Augustine ........................... 128/200.26 |
| 5,174,283 | 12/1992 | Parker ................................. 128/200.26 |
| 5,203,320 | 4/1993 | Augustine ................................. 128/10 |
| 5,277,178 | 1/1994 | Dingley .............................. 128/200.26 |
| 5,303,697 | 4/1994 | Brain ................................. 128/200.26 |
| 5,318,009 | 6/1994 | Robinson ................................. 128/16 |
| 5,339,805 | 8/1994 | Parker ................................. 128/200.26 |
| 5,391,248 | 2/1995 | Brain ................................... 156/242 |
| 5,425,356 | 6/1995 | Ough ....................................... 128/11 |
| 5,507,279 | 4/1996 | Fortune et al. ..................... 128/200.26 |
| 5,529,582 | 6/1996 | Fukuhara ................................ 606/205 |
| 5,623,921 | 4/1997 | Kinsinger et al. ................ 128/200.26 |
| 5,682,880 | 11/1997 | Brain ................................. 128/207.15 |
| 5,743,254 | 4/1998 | Parker ................................. 128/200.26 |
| 5,746,202 | 5/1998 | Pagan ................................. 128/207.14 |

OTHER PUBLICATIONS

Pinosky, "Laryngeal Mask Airway: Uses in Anesthesiology" (Article), Jun. 1996, SMJ, pp. 1–7.

*Primary Examiner*—Aaron J. Lewis
*Attorney, Agent, or Firm*—Hodgson, Russ, Andrews, Woods & Goodyear, LLP

[57] ABSTRACT

In a hand tool for facilitating the introduction of a laryngeal mask into a patient. A hand tool insertable into a patient, the hand tool for engaging a laryngeal mask and having a pivot region. The hand tool engages the laryngeal mask, and when the hand tool is pivoted, the hand tool raises the mask from the back of the throat to permit proper insertion of the mask into the patient.

9 Claims, 4 Drawing Sheets

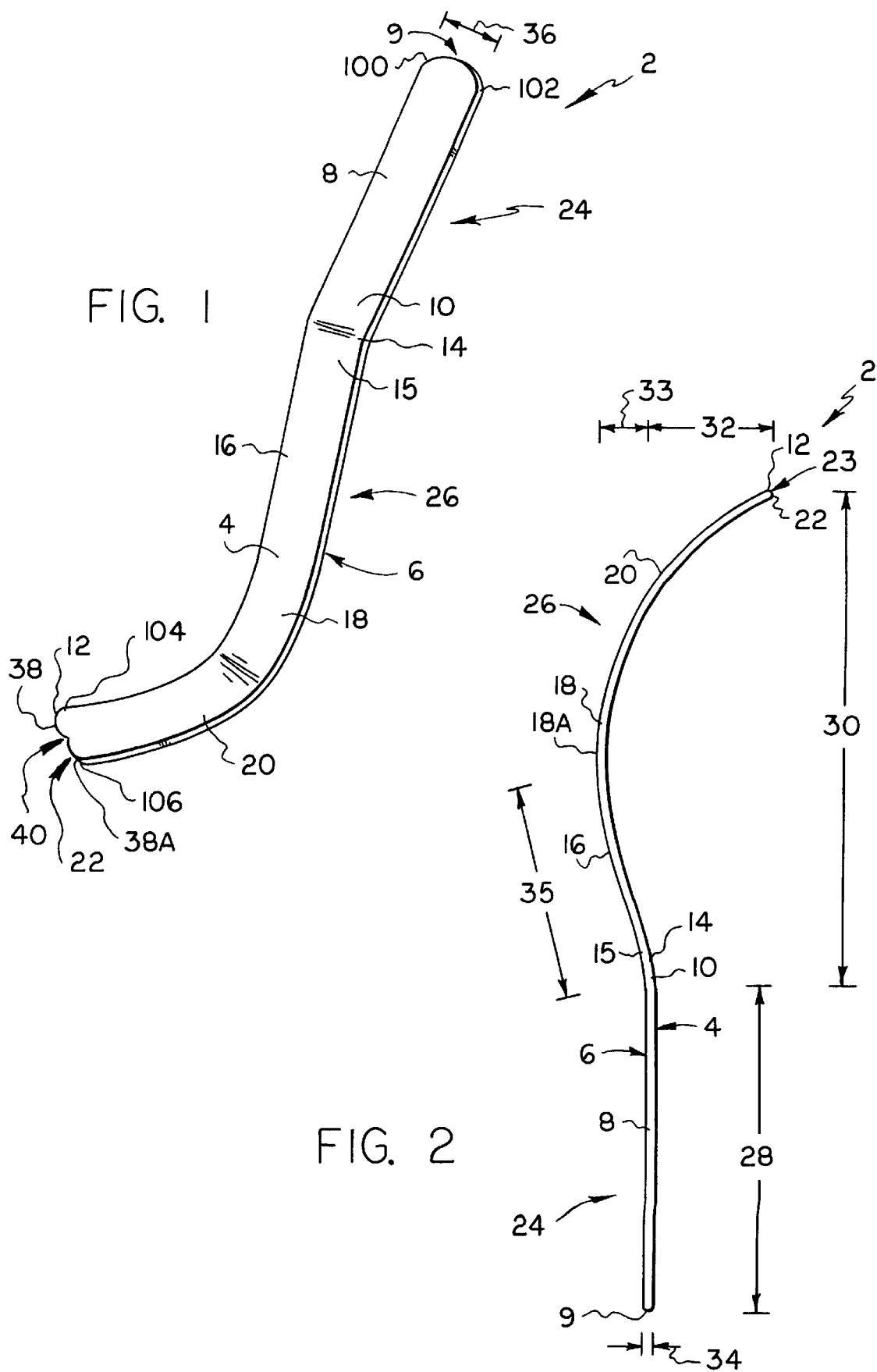

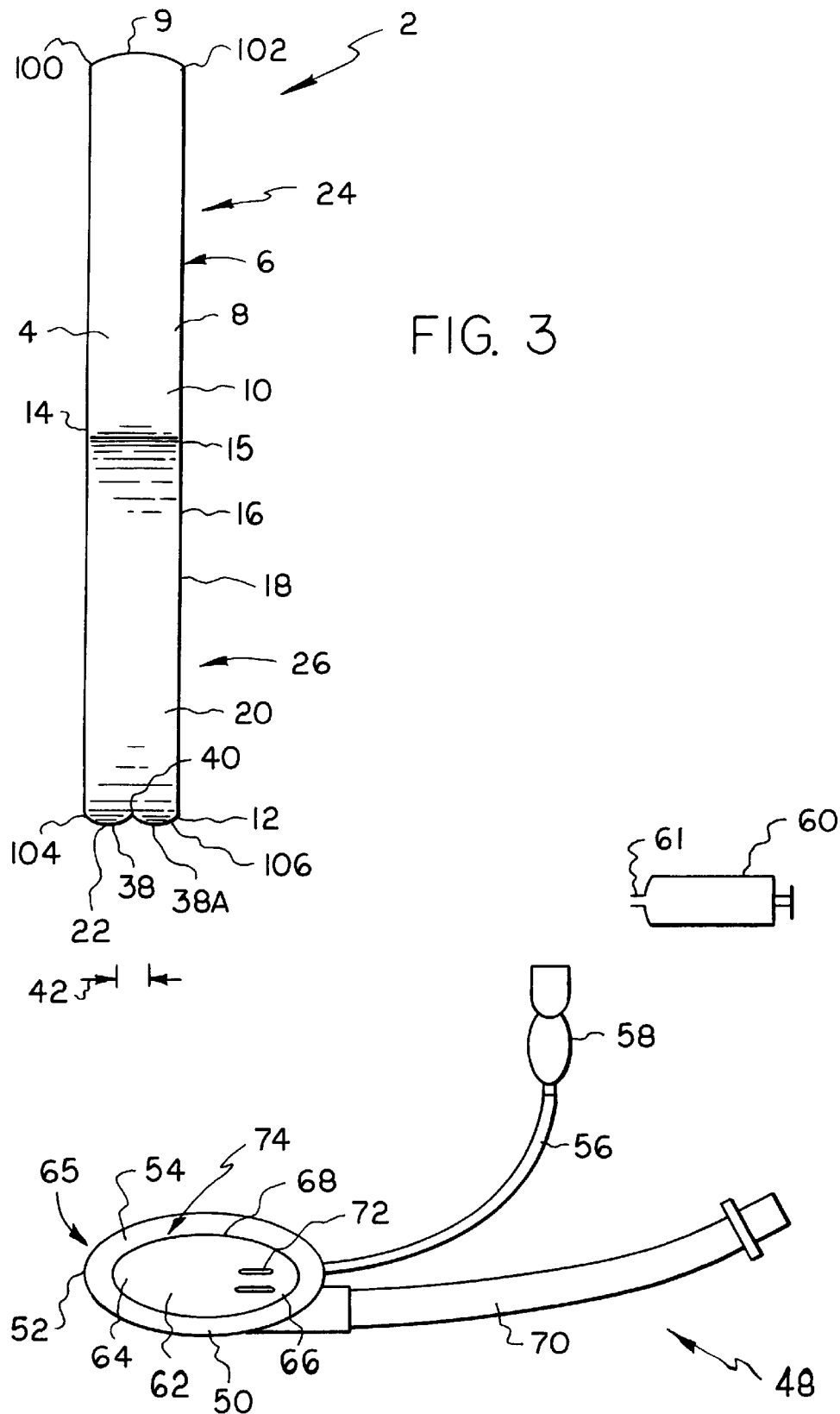

HAND TOOL FOR INTRODUCING A LARYNGEAL MASK

BACKGROUND OF THE INVENTION

1. Field of the Invention

The present invention relates generally to hand held medical tools, and with more particularity, to a hand held medical tool to facilitate the introduction of a laryngeal mask airway into a patient.

2. Prior Art

Laryngeal mask airways, also called laryngeal masks, are presently used to establish an airway in a patient during general anesthesia. The laryngeal mask is inserted blindly into the pharynx, until it reaches and engages the upper esophageal sphincter, at which point a balloon portion of the mask is inflated, which forms a low pressure seal over the laryngeal inlet. Laryngeal masks are more efficient than standard face masks which may not form tight seals with the patient's face, permitting anaesthesia to escape therebetween. Laryngeal masks are thus becoming increasingly more popular. However, laryngeal masks are difficult to insert and properly position in the pharynx, because the masks are large, and the tip of the mask tends to bend upon itself when forced around the back of the throat inhibiting the proper placement of the mask.

Presently, physicians insert a laryngeal mask into a patient by using their fingers. In this manual insertion method, the laryngeal mask is forced into a patient's mouth behind the tongue, and then forced into the pharynx with the aid of the physician's index finger, which is pushed deeply into the patient's throat. This procedure has been known to result in damage to the soft tissues of the patient's throat. This procedure also poses a significant risk to the physician of contracting a contagious disease, such as HIV, since allergic reactions to latex prevent the physician from using latex gloves in all instances, and even if latex gloves are used, they can be easily punctured by teeth and braces. Further, the manual method becomes extremely difficult to perform when the patient is an infant, as the infant's mouth is simply too small to accommodate adult fingers.

Another device used to aid in the insertion of laryngeal masks is found in U.S. Pat. No. 5,277,178 to Dingley. The patent shows a thin flexible plastic channel slide placed within the patient's throat, and the laryngeal mask is supposed to slide over the slide around the back of the throat. The drawback with this device is that it still makes insertion of the laryngeal mask very difficult, as the tip of the laryngeal mask still turns upon itself when it is inserted and has to bend around the back of the throat. The device is so thin it actually bends as the laryngeal mask slides over it, which is conducive to the tip of the laryngeal mask turning upon itself, thus preventing the mask from being advanced.

Another drawback of the slide device found in U.S. Pat. No. 5,277,178 is that it is a passive device, providing the physician with no effective way to actively control and guide the laryngeal mask.

Hence, there is a great need for a device and methodology for using same to enable a physician to safely and quickly introduce a laryngeal mask.

The present invention provides a novel solution to the problem of inserting laryngeal mask airways, having none of the drawbacks and disadvantages of the procedures and devices presently in use.

SUMMARY OF THE INVENTION

It is an objective of the present invention to provide a hand tool to guide the placement of a laryngeal mask.

It is an objective of the present invention to provide a hand tool for introducing a laryngeal mask which allows the physician to independently and without assistance insert a laryngeal mask.

It is an objective of the present invention to provide a hand tool which is rigid and which has an engaging means for actively engaging a laryngeal mask.

It is an objective of the present invention to provide a hand tool for introducing a laryngeal mask which may be disposable.

It is an objective of the present invention to provide a hand tool for introducing a laryngeal mask which may be reused.

It is an objective of the present invention to provide a hand tool for introducing a laryngeal mask which decreases the risk to the physician introducing the mask of being exposed to contagious diseases.

It is an objective of the present invention to provide a hand tool which includes a pivot portion to be used to actively raise and lower a laryngeal mask in order to facilitate its introduction into the patient.

It is an objective of the present invention to provide a method for making and using a reusable hand tool for introducing a laryngeal mask into a patient.

It is an objective of the present invention to provide a kit having a laryngeal mask and a hand tool for introducing same into a patient.

Various other objects and advantages of the present invention will appear from the following description of the embodiments of the present invention, and the novel features will be particularly pointed out hereinafter in connection with the appended claims.

The present invention is a hand tool having a handle portion and an insertion portion, both of these portions having a first and second end. The second end of the handle portion is merged to the second end of the insertion portion at a junction. The insertion portion is constructed so as to comprise an offset ramp, a pivot region, and an arcuate region. An engaging means is positioned at the first end of the insertion portion. The hand tool may be constructed out of stainless steel and be reusable, or may be constructed out of rigid plastic or other suitable material so as to be disposable.

Generally, to use the tool, the physician first inserts the tool in the patient's mouth and depresses the patient's tongue with the tool, so as to make room in the mouth for the laryngeal mask, but this step may not be required for all patients. Next, a deflated laryngeal mask is inserted into the patient's mouth, until it contacts the back of the patient's throat. The insertion portion of the hand tool is then removed from the mouth and reinserted into the patient's mouth between the palate and the laryngeal mask, such that the pivot portion contacts with the patient's palate. The physician then grips the handle with one hand so as to controllably manipulate the engaging means such that it releasably engages with the laryngeal mask. Once the engaging means engages with the laryngeal mask, the physician then forces on the handle. This causes the insertion portion to pivot about the pivot region, and simultaneously causes the pivot portion to raise the engaging means, which raises the lower end of laryngeal mask, so that the tip of the mask does not contact the back of the throat. The physician then urges on the laryngeal mask with his or her other hand to advance it into the throat, and continues raising the mask with the hand tool until the laryngeal mask engages the upper esophageal sphincter. The hand tool is then removed from the patient, and the laryngeal mask is inflated.

These and other novel features of the present invention will be readily apparent from the following detailed description and appended drawings and claims.

BRIEF DESCRIPTION OF THE DRAWINGS

The appended drawings show the following:

FIG. 1 is a perspective view of the laryngeal hand tool.

FIG. 2 is a side elevational view of the laryngeal hand tool.

FIG. 3 is a plan view of the laryngeal hand tool.

FIG. 4 is a perspective view of the laryngeal mask airway, and pump for inflating same.

DETAILED DESCRIPTION OF THE PREFERRED EMBODIMENTS

Figure 5:
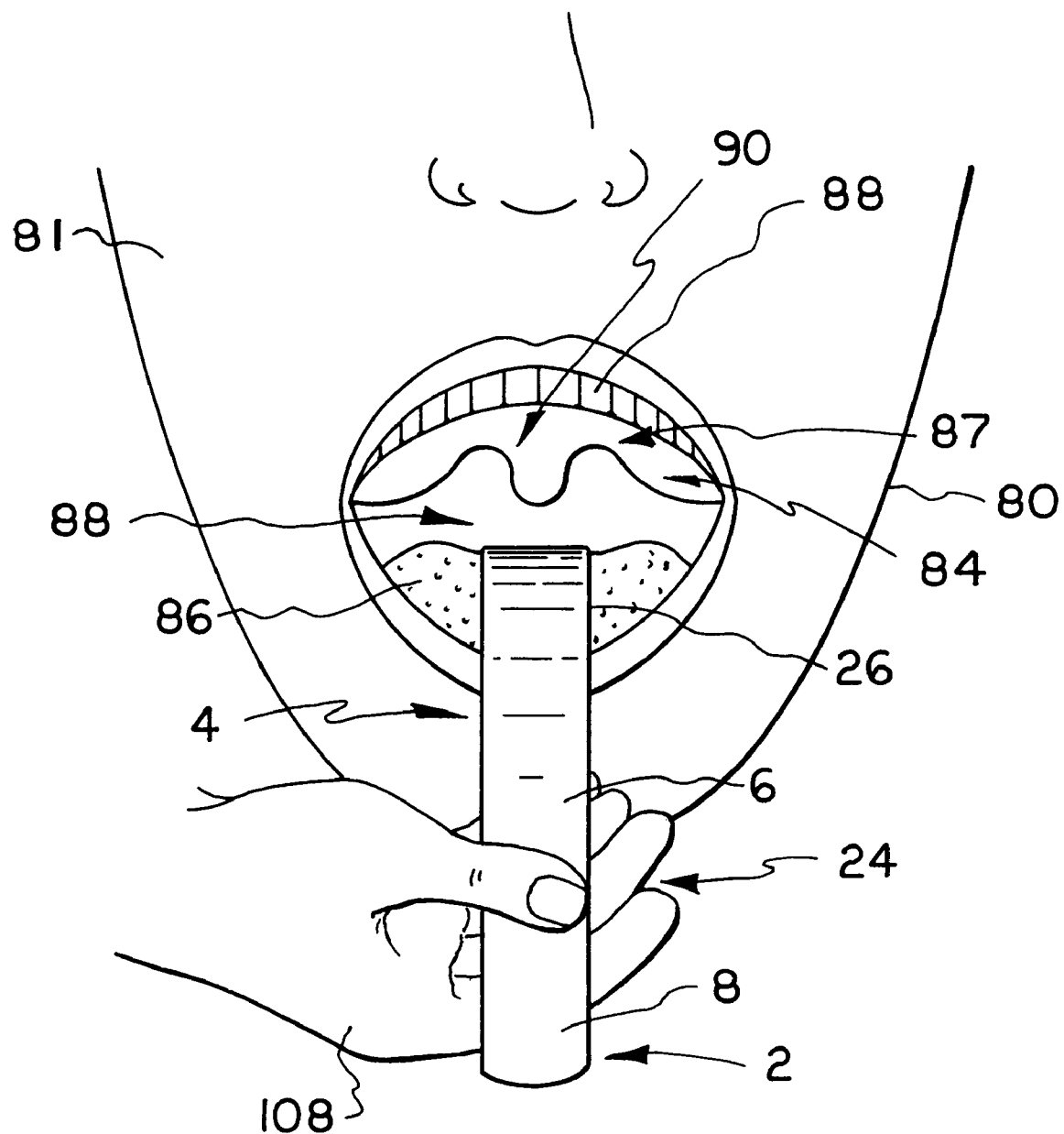
FIG. 5 is a plan view showing the laryngeal hand tool inserted into the patient's mouth depressing the tongue to make room for the laryngeal mask.

Turning now to FIG. 1, seen therein is a perspective view of the present invention, laryngeal hand tool 2. Hand tool 2 may be completely formed, as fully described and set forth below, from a blank, which may be an elongated body having a rectangular shape, cut out from a sheet of a stock material. The stock material is desirably stiff, so as to resist bending when hand tool 2 is used. For reusable embodiments of the present invention, the stock material may be surgical grade stainless steels and the like, and for disposable embodiments of the present invention the stock material may comprise stiff plastics and the like, and other similarly suitable materials known to those skilled in the art.

The hand tool 2 is constructed so as to have a handle portion 24 which comprises a handle 8, a first end 9, and a second end 10. Handle 8 has a generally rectangular shape, and has smooth rounded corners 100 and 102 at the first end 9. Handle 8 may be about 7–8 cm long, and this length, designated 28, is seen in FIG. 2. The handle 8 also has a width, designated 36 and seen in FIG. 1, which may be about 2–3 cm. The thickness of handle 8, designated 34 and seen in FIG. 2, may be about 2–3 mm. The entire hand tool 2 may be constructed so that the width 36 and thickness 34 may be essentially constant throughout all portions of entire hand tool 2.

The present invention is not limited to handle 8 comprising a generally rectangular shape, and other embodiments of handle 8 are within the scope of the present invention. For example, handle 8 may be embodied so as to have an hourglass shape, an enlarge portion for gripping, an ergonomically comfortable shape, or any other suitable shape. Of course, in such embodiments, the width 36 and thickness 34 of hand tool 2 would not be constant throughout all portions thereof.

Hand tool 2 also comprises an insertion portion 26, formed such that it has a first end 12 and a second end 15, as seen in FIGS. 1–2. The second end 10 of handle portion 24 merges with the second end 15 of the insertion portion 26, along a junction 14. Junction 14 may be as simple as a bend in the material if hand tool 2 is formed from an elongated body, as previously described.

Insertion portion 26 is formed to have an offset ramp 16, a pivot region 18, and an arcuate region 20. One end of the offset ramp 16 corresponds to the second end 15 of the insertion portion 26, and merges with the handle portion 24 along junction 14. The other end of the ramp 16 merges with one end of pivot region 18, and the other end of pivot region 18 merges with one end of arcuate region 20. The other end of the arcuate region 20 corresponds with the first end 12 of insertion portion 26. Offset ramp 16 has a generally flat rectangular shape, and pivot region 18 and arcuate region 20 have generally curved shapes. The shape of the pivot region may be in the form of the letter C, and the shape of arcuate region 20 may be in the form of a flattened letter C.

Insertion portion 26 may have a length measured linearly from first end 12 to second end 15, designated 30 in FIG. 2, of about 10–11 cm. The offset ramp 16 may have a length, designated 35 in FIG. 2, of 3.5–4.5 cm. A plane is defined by the length designated 28 and width designated 36 of handle 8. The fulcrum 18A of pivot region 18 is offset from the plane defined by handle 8 by a distance, designated 33 in FIG. 2, which may be about 1–1.5 cm. The first end 12 of arcuate region 26 is also offset from this plane defined by handle 8 by a distance, designated 32 in FIG. 2, which may be about 2–3 cm. The first end 12 of arcuate region 26 and the fulcrum 18A are located on opposite sides of the plane defined by length 28 and width 36 of handle 8.

Hand tool 2 has formed at the first end 12 an engaging means 22, seen in FIG. 3. Engaging means 22 may be formed integrally with the body of the arcuate region 20 of the insertion portion 26 found at first end 12, so as to reduce costs of manufacturing the engaging means 22. Engaging means 22 is for engaging with the laryngeal mask 48, and may be embodied in a variety of different shapes and sizes. For example, engaging means 22 may be a smooth surface 23 running along first end 12 of the insertion portion 26 as in FIG. 2. Also, as seen in FIGS. 1 and 3, engaging means 22 may be shaped to have first and second shoulders 38 and 38A, respectively, extending from the first end 12. The first and second shoulders 38 and 38A defining a notch 40 therebetween. Notch 40 may be constructed such that it has a width, designated 42 in FIG. 3, of about 1–3 mm. Such an engaging means 22 could be formed by simply notching the first end 12 of the insertion portion 26 to form the first and second shoulders 38 and 38A, such notching procedures known to those skilled in the art. In any embodiment of engaging means 22 utilized, sharp corners at first end 12 are not desirable, as they could increase the risk of cutting the patient, thus first end 12 of the insertion portion 26 is fabricated to have smooth corners 104 and 106.

With hand tool 2 so constructed, it has a top surface 4 and on the opposite side thereof a bottom surface 6. Top surface 4, best seen in FIG. 1, is the surface of the tool which will contact the laryngeal mask 48, and bottom surface 6 is the side of hand tool 2 which will contact the palate 90 of patient 80, as fully described below.

To construct hand tool 2 thus far might entail taking a blank, which may be in the shape of an elongated body having a rectangular shape, cut from a suitable sheet of stock material, for example stainless steel, and bending the blank until the above described features are formed at the above described locations. Then the features of the engaging means 22 could be machined into first end 12 of arcuate region 26 of hand tool 2. Disposable embodiments of hand tool 2 may be constructed by the blow molding or injection molding of thermo-plastics or resins, and the extrusion or pressure molding of thermosetting plastics or resins to accomplish the shapes described above. Of course, other construction materials and methods of fabrication of will be readily apparent to one skilled in the art in view of the detailed description and appended drawings and claims. These are all within the scope of the present invention.

The numerous attributes of the above described features of hand tool 2 become apparent when hand tool 2 is used to introduce a laryngeal mask 48, best seen in FIG. 4, into the patient 80 seen in FIG. 5. Before fully describing this procedure, background information on the structure of a laryngeal mask 48 is appropriate.

The laryngeal masks 48 presently comes in about six different sizes, each size designed to fit properly in particular sized patient, from new born infants to adults. The laryngeal mask 48, best seen in FIG. 4, has a balloon portion seen at 50 having a tip 52 and a sealing surface 54. An inflation tube at 56 is in fluid communication with balloon 50, and with a valve 58. The nozzle 61 of hand pump 60, shown in FIG. 4, which may also be embodied as a syringe, is connectably insertable into valve 58, and when so connected, balloon 50 may be inflated or deflated as desired. Valve 58 prevents air from leaving or entering the balloon 50 when the hand pump 60 is not connected thereto.

Balloon portion 50 surrounds a generally elliptical spoon shaped rigid member 62. The rigid member 62 comprises a proximal portion 64, a distal portion 66, a gas side 68, and an engaging side 65 opposite thereto. Also, a gas tube 70 connects to the distal portion 66 of rigid member 62. Gas tube 70 is for delivering anesthesia and other gases to the patient 80, and for removing gases exhaled by the patient 80, said gas and anaesthesia travel through the gas ports 72 formed in the distal portion 66 of rigid member 62. Laryngeal mask 48 also has a sealing side designated 74 which comprises the sealing surface 54 of balloon 50 and the gas side 68 of rigid member 62. Sealing side 74 of the mask 48 is for forming a low pressure seal with the laryngeal inlet 82 of patient 80.

Figure 6:
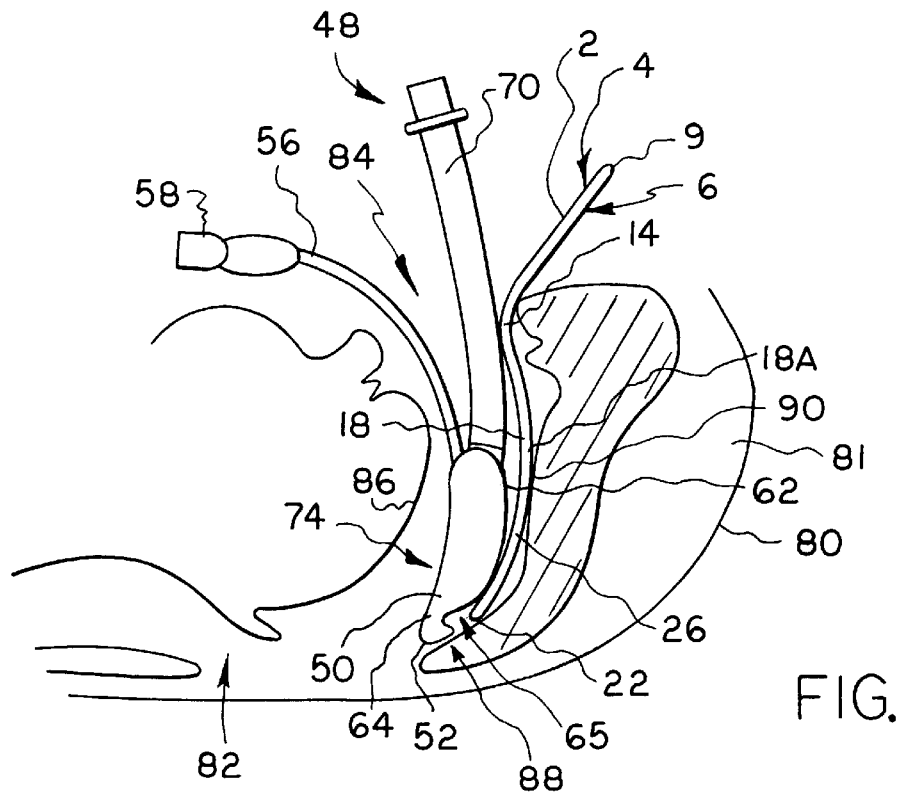
FIG. 6 is a crossectional view of the laryngeal hand tool inserted into the patient's throat.

Turning to FIGS. 5–6, the method for using hand tool 2 is seen. Patient 80 is positioned flat out on his or her back, the head 81 is held at a slight extension, and the mouth 84 is opened. The first end 12 of the insertion portion 26 of hand tool 2 is first inserted into the patient's 80 mouth 84, with the handle portion 24 held by the physician's hand 108, as seen in FIG. 5. Note that at this point, the top surface 4 of hand tool 2 is pressed against the tongue 86, and forces tongue 86 away from teeth 88, thus maintaining an open area, designated 87 in FIG. 5, in the mouth 84. The open area 87 for accommodating the laryngeal mask 48. While maintaining this position with one hand, the balloon 50 and rigid member 62 of laryngeal mask 48 are inserted into the mouth 84, tip 52 first, with the other hand (not shown), such that the sealing side 74 contacts with and moves over tongue 86 and the bottom surface 6 of hand tool 2. At this point, the laryngeal mask 48 is generally found between tongue 86 and palate 90. Of course, the balloon 50 is deflated during the initial insertion, so as to decrease the size of the laryngeal mask 48, thus facilitating insertion. In any event, laryngeal mask 48 is inserted until it reaches and contacts the back of the throat 88. It is noted that the first step described above, using hand tool 2 to force tongue 86 away from teeth 88 to maintain open area 87, may not be required for all patients 80.

At this point of the insertion of the laryngeal mask 48 into patient 80, the problem the present invention solves is best seen in FIG. 6. The tip 52 of balloon 50 is seen folded upon itself at the back of throat 88, such that the laryngeal mask 48 cannot be safely advanced, and any attempts to insert the laryngeal mask 48 would result in both trauma to the patient 80, and an inadequate seal forming when the balloon 50 was ultimately inflated when against the laryngeal inlet 82.

To resolve the problem of the tip 52 of balloon 50 being folded upon itself, the physician next takes hand tool 2 completely out of the patient's 80 mouth 84, and reinserts hand tool 2 into mouth 84 as seen in FIG. 6. The first end 12 of insertion portion 26 of hand tool 2 is first inserted into mouth 84, such that the top surface 4 of hand tool 2 contacts laryngeal mask 48, and bottom surface 6 contacts palate 90 as seen in FIG. 6. The physician then takes the handle 8 of hand tool 2, and manipulates the engaging means 22 such as to move the engaging means 22 into contact with the engaging surface 65 of rigid member 62 along the proximal portion 64 thereof, as seen in FIG. 6

While engaging means 22 is brought into contact with the engaging surface 65 of the proximal portion 64 of rigid member 62 of the laryngeal mask 48, the physician positions the fulcrum 18A of pivot region 18 of hand tool 2 against the palate 90. The physician then forces handle 8 towards the palate 90, which in turn causes the hand tool 8 to pivot about the fulcrum 18A, which moves engaging means 22 away from the back of the throat 88. Since the engaging means 22 is engaged with the engaging surface 65 of rigid member 62 along the proximal portion 64 thereof, the rigid member 62 and balloon 50 lift off and away from the back of the throat 88. This causes the tip 52 to lift off the back of the throat 88 and become unfolded, eliminating the problems previously discussed.

Figure 7:
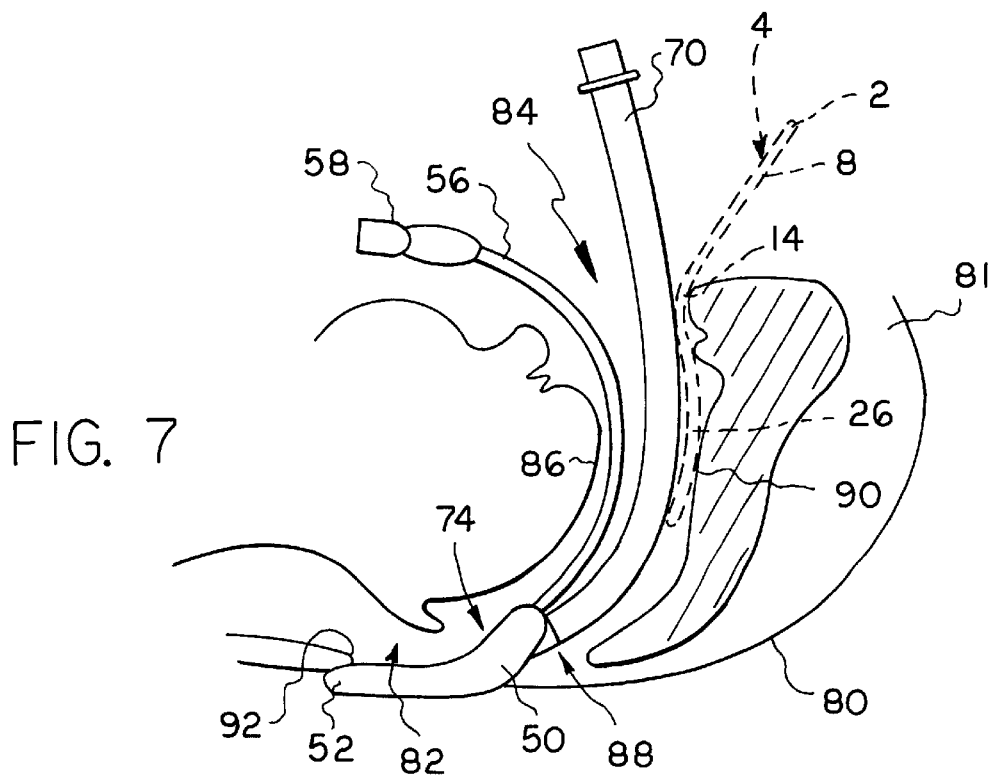
FIG. 7 is a crossectional view of the laryngeal mask in its final position.

The physician simultaneously advances the laryngeal mask 48 deeper into the throat, and continues lifting and feeding the laryngeal mask 48 with hand tool 2, until the laryngeal mask 48 contacts with the esophageal sphincter 92, which is illustrated in FIG. 7. Hand tool 2 is then removed, and balloon 50 is inflated so that a seal is formed with the laryngeal mask 48 and the laryngeal inlet 82. Hand tool 2 may be reused, if embodied as a reusable unit, once it is properly cleaned in accordance with procedures known to those skilled in the art. If hand tool 2 is embodied as a disposable unit, it may be discarded.

To remove the laryngeal mask 48, the balloon 50 is deflated, as described above, and the laryngeal mask 48 is pulled out the mouth 84, hand tool 2 not being required in the removal process.

The present invention also provides a safety feature contained within the very structure of hand tool 2. It is desirable that hand tool 2 only be inserted into the patient 80 to a point which is not dangerous to the patient 80. If hand tool 2 is inserted too far into patient 80, patient 80 could be injured. Thus, junction 14 serves as an indicator to the physician, indicating how much of the insertion portion 26 is located internally to the patient 80. The physician should monitor junction 14, and if junction 14 aligns with teeth 88, the physician should conclude that no more of the hand tool 2 may be safely inserted into the patient 80.

There are modifications of hand tool 2 which are also within the scope of the present invention. The size of hand tool 2, and all of the dimensions specifically set forth above, may be adjusted for different sized hand tools 2. For small patients 80, such as infants, hand tool 2 would be properly dimensioned, such that it could be accommodated in the infant's mouth for the above described purposes. Also, the engaging means 22 may be dimensioned to accommodate the different sized laryngeal masks which presently exist.

The present invention also provides a methodology for constructing a hand tool 2, and a methodology of using the hand tool 2 to introduce a laryngeal mask 48 into a patient 80, as fully described.

In conjunction with the hand tool 2 fully described herein, and the methodology for making and using same, it may be desirable to have hand tool 2 and the laryngeal mask 48 available in kit form. For example, an appropriately dimensioned hand tool 2 might be packaged with an appropriately sized laryngeal mask 48 in a convenient hermetically sealed package, openable only when needed, and fully disposable after used. The kit might additionally comprise therein a pump 60 for inflating the balloon 50 on the laryngeal mask 48. Of course, other embodiments of the kit described herein will be readily apparent to one skilled in the art in view of the detailed description, drawings and claims of the present invention, and these other kit embodiments are within the scope of the present invention.

Thus, the present invention satisfies all of the objectives previously set forth, in that is provides a hand tool 2 which decreases the risk to the physician of contracting a contagious disease, may be embodied to be a reusable tool, and greatly facilitates the introduction of a laryngeal mask 48 into a patient 80, and permits a physician, without assistance, to insert a laryngeal mask 48.

It will be understood that various changes in the details, materials, steps, and arrangement of parts, which have been herein described and illustrated in order to describe the nature of the invention, may be made by those skilled in the art within the principle and scope of the present invention as expressed in the appended claims.

What is claimed is:

1. A hand tool for introducing a laryngeal mask through a patient's mouth, the laryngeal mask having a rigid member with a proximal portion and an engaging side and having a balloon with a tip, the balloon surrounding the rigid member, the hand tool comprising:

an insertion portion having a first end and a second end, the insertion portion for insertion into the mouth;

a handle portion having a first end and a second end, the second end of the handle portion merged with the second end of the insertion portion;

an engaging means on the first end of the insertion portion, the engaging means for releasably engaging the engaging side of the rigid member along the proximal portion for preventing the tip of the balloon from folding upon itself and facilitating the insertion of the laryngeal mask into the patient.

2. The hand tool according to claim 1, wherein the engaging means comprises a smooth surface, the smooth surface for engaging with and lifting the laryngeal mask and permitting the laryngeal mask to be slid thereover into the patient.

3. The hand tool according to claim 1, wherein the engaging means comprises a first shoulder and a second shoulder, the first shoulder and the second shoulder defining a notch therebetween, the notch for engaging with and lifting the laryngeal mask and permitting the laryngeal mask to be slid thereover into the patient.

4. The hand tool according to claim 1, wherein the engaging means is formed from the first end of the insertion portion of the hand tool.

5. The hand tool according to claim 1, wherein the insertion portion further includes:

an offset ramp having ends;

a pivot region having ends; and an arcuate region having ends, one end of the offset ramp corresponding with the second end of the insertion portion, the other end of the offset ramp merged with the pivot region, and the other end of the pivot region merged with one end of the arcuate region, and the other end of the arcuate region corresponding with the first end of the insertion portion.

6. The hand tool according to claim 5, wherein the pivot region has a curved shape, the arcuate region has a curved shape, and the offset ramp is flat.

7. The hand tool according to claim 6, wherein the curved shape of the pivot region has a first radius, and the curved shape of the arcuate region has a second radius that is greater than the first radius.

8. A kit for introducing a laryngeal mask through a patient's mouth, the laryngeal mask having a rigid member with a proximal portion and an engaging side, and having a balloon with a tip, the balloon surrounding the rigid member, the kit comprising:

the laryngeal mask;

a hand tool comprising an insertion portion having a first end and a second end, the insertion portion for insertion into the mouth;

the hand tool further comprising a handle portion having a first end and a second end, the second end of the handle portion merged with the second end of the insertion portion, the handle portion for permitting the hand tool to be holdably controlled;

the hand tool further comprising an engaging means on the first end of the insertion portion, the engaging means for releasably engaging the engaging side of the rigid member along the proximal portion for preventing the tip of the balloon from folding upon itself, and facilitating the insertion of the laryngeal mask into the patient.

9. In combination:

a laryngeal mask capable of being inserted through a patient's mouth, the laryngeal mask having a rigid member with a proximal portion and an engaging side and having a balloon with a tip, the balloon surrounding the rigid member; and, a hand tool comprising an insertion portion having a first end and a second end, the insertion portion for insertion into the mouth; a handle portion having a first end and a second end, the second end of the handle portion merged with the second end of the insertion portion, an engaging means on the first end of the insertion portion, the engaging means for releasably engaging the engaging side of the rigid member along the proximal portion for preventing the tip of the balloon from folding upon itself and facilitating the insertion of the laryngeal mask into the patient.

* * * * *